United States Patent
Yuan et al.

(10) Patent No.: US 10,792,391 B2
(45) Date of Patent: Oct. 6, 2020

(54) BIODEGRADABLE MAGNESIUM ALLOY NERVE CONDUIT FOR NERVE DEFECT REPAIR AND ITS PREPARATION METHOD

(71) Applicants: SHANGHAI JIAO TONG UNIVERSITY, Shanghai (CN); SHANGDONG ZHONGBAOKANG MEDICAL DEVICES CO., LTD, Zibo, Shandong (CN)

(72) Inventors: Guangyin Yuan, Shanghai (CN); Wenjiang Ding, Shanghai (CN)

(73) Assignees: SHANGHAI JIAO TONG UNIVERSITY, Shanghai (CN); SHANGDONG ZHONGBAOKANG MEDICAL DEVICES CO., LTD, Zibo, Shandong (CN)

( * ) Notice: Subject to any disclaimer, the term of this patent is extended or adjusted under 35 U.S.C. 154(b) by 594 days.

(21) Appl. No.: 15/775,008

(22) PCT Filed: Jun. 27, 2014

(86) PCT No.: PCT/CN2014/080937
§ 371 (c)(1),
(2) Date: May 10, 2018

(87) PCT Pub. No.: WO2015/188403
PCT Pub. Date: Dec. 17, 2015

(65) Prior Publication Data
US 2019/0022276 A1    Jan. 24, 2019

(30) Foreign Application Priority Data

Jun. 11, 2014 (CN) .......................... 2014 1 0258445

(51) Int. Cl.
*A61L 27/04* (2006.01)
*A61L 27/56* (2006.01)
(Continued)

(52) U.S. Cl.
CPC ........ *A61L 27/047* (2013.01); *A61B 17/1128* (2013.01); *A61L 27/56* (2013.01);
(Continued)

(58) Field of Classification Search
CPC .................. A61F 2/04; A61B 17/1128; A61B 2017/00004; A61B 2017/1132;
(Continued)

(56) References Cited

U.S. PATENT DOCUMENTS

2005/0033418 A1* 2/2005 Banas ....................... A61F 2/06
                                                          623/1.49
2007/0010831 A1* 1/2007 Romero-Ortega ..........................
                                                          A61B 17/1128
                                                          606/152

(Continued)

*Primary Examiner* — Katrina M Stransky

(57) ABSTRACT

A biodegradable magnesium alloy nerve conduit for nerve defect repair has multiple lines of through holes in the tube wall thereof, the through holes in each line are axially arranged along a circular tube at equal distances, and the through holes in adjacent lines are arranged in a staggered way. A method for preparing the nerve conduit includes steps of: (step 1) processing a 45-degree conical surface at one end of a magnesium alloy tube blank, carrying out extrusion, and obtaining a magnesium alloy intermediate tube material; (step 2) obtaining a capillary tube after carrying out multi-pass rolling and drawing on the magnesium alloy intermediate tube material; (step 3) carrying out stress relief annealing on the capillary tube, laser cutting and punching, and obtaining a porous conduit; and (step 4) carrying out acid pickling on the porous conduit, and then carrying out electrochemical polishing treatment, and obtaining the nerve conduit.

2 Claims, 2 Drawing Sheets

(51) Int. Cl.
*A61B 17/11* (2006.01)
*A61L 27/58* (2006.01)
*A61B 17/00* (2006.01)
*C22F 1/06* (2006.01)

(52) U.S. Cl.
CPC ..... *A61L 27/58* (2013.01); *A61B 2017/00004* (2013.01); *A61B 2017/1132* (2013.01); *A61L 2430/32* (2013.01); *C22F 1/06* (2013.01)

(58) Field of Classification Search
CPC ............ A61B 17/11; A61B 2017/1103; A61B 2017/1107; A61B 2017/1121; A61B 2017/1135; A61B 2017/1139; A61B 2017/1142; A61B 17/1146; A61B 17/12
See application file for complete search history.

(56) References Cited

U.S. PATENT DOCUMENTS

| 2007/0077163 | A1* | 4/2007 | Furst | B22F 5/003 419/28 |
| 2007/0100358 | A2* | 5/2007 | Romero-Ortega | A61L 31/129 606/152 |

* cited by examiner

BIODEGRADABLE MAGNESIUM ALLOY NERVE CONDUIT FOR NERVE DEFECT REPAIR AND ITS PREPARATION METHOD

CROSS REFERENCE OF RELATED APPLICATION

This is a U.S. National Stage under 35 U.S.C 371 of the International Application PCT/CN2014/080937, filed Jun. 27, 2014, which claims priority under 35 U.S.C. 119(a-d) to CN 201410258445.X, filed Jun. 11, 2014.

BACKGROUND OF THE PRESENT INVENTION

Field of Invention

The present invention relates to the field of biological material processing, and in particular to a biodegradable magnesium alloy nerve conduit for nerve defect repair and its preparation method.

Description of Related Arts

Materials for repairing the peripheral nerve defect include autologous tissue (such as nerves, blood vessels and acellular matrix), but the autologous tissue has limited sources and may cause permanent damage to the donor site. The most promising method is to bridge and repair the nerve defect with the tissue engineered artificial nerve constructed by conduit. Currently, the conduit used in nerve repair is mainly concentrated in polymer and natural biological materials (e.g., collagen). Although these materials have excellent biocompatibility, the degradation products easily lead to the inflammatory response of surrounding tissue and wall collapse, the tube wall permeability is poor and it is difficult to accurately control the degradation time, which are not conducive to the regeneration of the nerve axons. Therefore, in clinical practice, no ideal nerve conduit material has been widely used at present.

With the progress of material science, biodegradable metal magnesium alloy materials have been applied to human clinical trials as a vascular stent. Such metal materials not only have good biocompatibility, but also have suitable mechanical properties, strong wall supporting effect and controllable degradation rate; degradation products are essential elements of human body, with good biocompatibility. In recent years, studies have shown that magnesium ions released during the degradation of magnesium alloy have protective effect on apoptosis caused by nerve cell damage [References: Hasanein P. et al, *Oral magnesium administration prevents thermal hyperalgesia induced by diabetes in rats. Diabetes Res Clin Pract* (2006) 73 (1): 17-22]. At the same time, studies have shown that magnesium ions can improve neurological function and memory of rats damaged by external forces [References: Jeong S. M, et al. *Changes in magnesium concentration in the serum and cerebrospinal fluid of neuropathic rats. Acta Anaesthesiol Scand* (2006). 50 (2): 211-6]. Porous tissue-engineered metal tubular stents can be accurately prepared by using laser processing technology, to provide three-dimensional scaffolds for the growth of defective nerve cells. Moreover, the magnesium metal material has good conductivity; external electric field can be applied to the implanted magnesium alloy nerve conduit to electrically stimulate the nerve defect area and further induce the expression of nerve growth factor (NGF) in the injury area, thereby creating a microenvironment conducive to nerve regeneration, [References: Chen Hong, et al., *Effects of electrical stimulation on expression of nerve growth factor in audit rats with spinal cord injury, Chinese Journal of Rehabilitation Theory and Practice,* 2012, vol. 18, No. 1, pp. 33-36]. In addition, the degradation of magnesium alloy may cause a slightly alkaline environment in the local area of the human body, which will effectively suppress the growth of bacteria and achieve the purpose of antisepsis and anti-inflammation. However, the degradation of polymer polylactic acid materials usually causes a local acidic environment, which is not conducive to antisepsis and anti-inflammation. All of these are the significant advantages of biodegradable magnesium alloy that non-metallic materials (high-molecular polymers, natural biomaterials) clinically used for nerve defect repair do not have. From the above, the biodegradable magnesium-based conduit is a kind of nerve conduit material with prospects in clinic applications.

Based on these advantages, the present invention first proposes the application of biodegradable magnesium-based conduit, which is used as a nerve conduit for repairing peripheral nerve defects, to explore a new way of repairing artificial nerve defect by tissue Engineering.

SUMMARY OF THE PRESENT INVENTION

In view of the defects in the prior art, an object of the present invention is to provide a biodegradable magnesium alloy nerve conduit for nerve defect repair and its preparation method.

The present invention is realized by the following technical solutions:

In a first aspect, the present invention provides a biodegradable magnesium alloy nerve conduit for nerve defect repair, wherein the biodegradable magnesium alloy nerve conduit is in a circular tube shape, the biodegradable magnesium alloy nerve conduit has multiple lines of through holes in a tube wall thereof, the through holes in each line are axially arranged along a circular tube at equal distances, and the through holes in adjacent lines are arranged in a staggered way.

Preferably, a length of the nerve conduit is 5-50 mm, and a thickness of the nerve conduit is 0.1-0.2 mm.

Preferably, a porosity of the nerve conduit is 2%-20%, and an aperture of the through holes is 0.1-0.3 mm.

In a second aspect, the present invention also provides a method for preparing the biodegradable magnesium alloy nerve conduit for nerve defect repair, wherein the method comprises steps of:

(step 1) processing a 45-degree conical surface at one end of a magnesium alloy tube blank, carrying out extrusion, and obtaining a magnesium alloy intermediate tube material;

(step 2) obtaining a capillary tube after carrying out multi-pass rolling and drawing on the magnesium alloy intermediate tube material;

(step 3) carrying out stress relief annealing on the capillary tube, laser cutting and punching, and obtaining a porous conduit; and (step 4) carrying out acid pickling on the porous conduit in an ultrasound cleaning machine, and then carrying out electrochemical polishing treatment, and obtaining the biodegradable magnesium alloy nerve conduit for nerve defect repair.

Preferably, in the (step 1), an outer diameter of the magnesium alloy tube blank is Ø20 mm, an extrusion temperature is 300-400° C., and an outer diameter of the magnesium alloy intermediate tube material is Ø6-Ø8 mm, and a wall thickness is 0.5-1 mm; before extrusion, boron nitride spray is sprayed on a mold and inner and outer walls of the magnesium alloy tube blank as a lubricant.

Preferably, in the (step 2), an outer diameter of the capillary tube is 1-3 mm, and a wall thickness thereof is 0.1-0.2 mm.

Preferably, in the (step 3), a stress relief annealing temperature is 300-350° C., and an annealing time is 20-30 min.

Preferably, in the (step 4), the acid pickling is specifically as carrying out ultrasonic pickling in a pickling solution for 5-30 min.

Preferably, the pickling solution comprises 80-100 ml/L of phosphoric acid and 40-60 g/L of ammonium bifluoride; a solvent is deionized water.

Preferably, in the (step 4), a polishing solution used for the electrochemical polishing treatment comprises phosphoric acid and absolute ethanol with a volume ratio of 1:1 or comprises ethylene glycol monoethyl ether and hydrochloric acid with a volume ratio of 9:1; a polishing treatment voltage is 2-8V, a polishing treatment time is 20-240 s, and a polishing treatment temperature is room temperature.

Compared with the prior art, the present invention has the following beneficial effects:

(1) The preparation method of the present invention has simple process, and the porous biodegradable magnesium alloy nerve conduit for the nerve defect repair is uniform in wall thickness and smooth in surface.

(2) The biodegradable magnesium alloy nerve conduit for nerve defect repair of the present invention has the advantages of excellent biocompatibility, good supporting effect of lumen and good permeability of the perforated tube wall, so it is beneficial to the regeneration of the nerve axons; the present invention adopts a tissue engineered artificial nerve repair system constructed by porous biodegradable magnesium alloy nerve conduit to repair the nerve defect through bridging.

(3) The magnesium metal material used in the present invention has good conductivity; external electric field can be applied to the implanted magnesium alloy nerve conduit to electrically stimulate the nerve defect area and further induce the expression of nerve growth factor (NGF) in the injury area, thereby creating a microenvironment conducive to nerve regeneration.

(4) The degradation of magnesium alloy material used in the present invention may cause a weakly alkaline environment in the local micro-area of the human body; it is beneficial to inhibit the growth of bacteria and can achieve the purpose of antisepsis and anti-inflammation within a certain time after the operation.

(5) The tube wall of the biodegradable magnesium alloy nerve conduit for nerve defect repair in the present invention is uniformly distributed with a number of holes, which are conducive to the nutrient exchange between the damaged peripheral nerve and the surrounding tissues outside the tube wall; meanwhile, the conduit wall is distributed with a number of holes to regulate the degradation rate, which is beneficial to matching the time required for nerve regeneration with the conduit degradation time.

(6) The biodegradable magnesium alloy nerve conduit for nerve defect repair in the present invention adopts the biodegradable magnesium alloy material with suitable toughness, which can provide sufficient radial support strength to prevent the collapse of wall.

BRIEF DESCRIPTION OF THE DRAWINGS

Other features, objects, and advantages of the present invention will become more apparent from reading the description of non-limiting embodiments detailed with reference to the following drawings.

DETAILED DESCRIPTION OF THE PREFERRED EMBODIMENT

The present invention is described in detail as follows with reference to specific embodiments. The following embodiments will help provide further understanding of the present invention for those skilled in the art, and not in any way limit the present invention. It shall be noted that several variants and improvements can be made without departing from concept of the present invention for ordinary persons skilled in the art. All these fall within the protection scope of the disclosure.

First Embodiment

Figure 1:
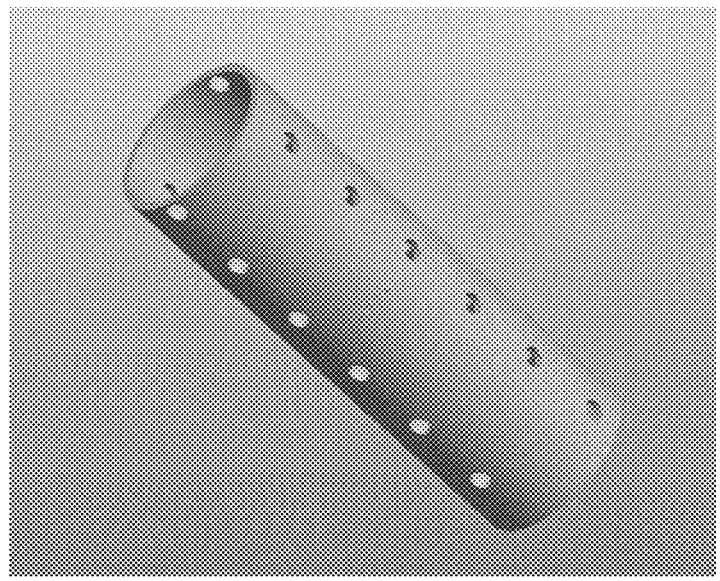
FIG. 1 is a 3D rendering of a biodegradable magnesium alloy nerve conduit for nerve defect repair in the present invention.

A biodegradable magnesium alloy nerve conduit for nerve defect repair according to a first embodiment is illustrated, as shown in FIG. 1, which is a circular tube with a length of 6 mm, an outer diameter of 2 mm and a wall thickness of 0.2 mm; wherein the biodegradable magnesium alloy nerve conduit has 4 lines of through holes in a tube wall thereof, the through holes in each line are axially arranged along the circular tube at equal distances, and the through holes in adjacent lines are arranged in a staggered way; an amount of the through holes in each line is 6, and an aperture thereof is 0.3 mm.

A method for preparing the biodegradable magnesium alloy nerve conduit for nerve defect repair according to the first embodiment is also illustrated, wherein the method comprises steps of:

(step 1) processing a 45-degree conical surface at one end of a Mg—Nd—Zn—Zr magnesium alloy tube blank with an outer diameter of 20 mm, carrying out extrusion at a temperature of 400° C., and obtaining a magnesium alloy intermediate tube material with a size of Ø8×0.5 mm (outer diameter×wall thickness);

(step 2) obtaining a capillary tube with an outer diameter of 2 mm and a wall thickness of 0.2 mm after carrying out multi-pass rolling and drawing on the magnesium alloy intermediate tube material;

(step 3) carrying out stress relief annealing on the capillary tube at a temperature of 300° C. for 30 min, laser cutting and punching, and obtaining a porous conduit; and (step 4) carrying out acid pickling on the porous conduit in an ultrasound cleaning machine for 5-30 min with a pickling solution which comprises 80-100 ml/L of phosphoric acid and 40-60 g/L of ammonium bifluoride, wherein a solvent is deionized water; and then carrying out electrochemical polishing treatment at room temperature with a polishing solution which comprises phosphoric acid and absolute ethanol with a volume ratio of 1:1, wherein a polishing treatment voltage is 2-8 V, a polishing treatment time is 20-240 s, and obtaining the biodegradable magnesium alloy nerve conduit for nerve defect repair.

Second Embodiment

A biodegradable magnesium alloy nerve conduit for nerve defect repair according to a second embodiment is illustrated, as shown in FIG. 1, which is in a circular tube with a length of 50 mm, a wall thickness of 0.15 mm and an outer diameter of 3 mm; wherein the biodegradable magnesium alloy nerve conduit has 8 lines of through holes in a tube wall thereof, the through holes in each line are axially arranged along the circular tube at equal distances, and the through holes in adjacent lines are arranged in a staggered way; an amount of the through holes in each line is 50, and an aperture thereof is 0.03 mm.

A method for preparing the biodegradable magnesium alloy nerve conduit for nerve defect repair according to the second embodiment is also illustrated, wherein the method comprises steps of:

(step 1) processing a 45-degree conical surface at one end of a Mg—Nd—Zn—Zr magnesium alloy tube blank with an outer diameter of 20 mm, carrying out extrusion at a temperature of 300° C., and obtaining a magnesium alloy intermediate tube material with a size of Ø7×0.8 mm (outer diameter×wall thickness);

(step 2) obtaining a capillary tube with an outer diameter of 3 mm and a wall thickness of 0.15 mm after carrying out multi-pass rolling and drawing on the magnesium alloy intermediate tube material;

(step 3) carrying out stress relief annealing on the capillary tube at a temperature of 350° C. for 20 min, laser cutting and punching, and obtaining a porous conduit; and (step 4) carrying out acid pickling on the porous conduit in an ultrasound cleaning machine for 5-30 min with a pickling solution which comprises 80-100 ml/L of phosphoric acid and 40-60 g/L of ammonium bifluoride, wherein a solvent is deionized water; and then carrying out electrochemical polishing treatment at room temperature with a polishing solution which comprises ethylene glycol monoethyl ether and hydrochloric acid with a volume ratio of 9:1, wherein a polishing treatment voltage is 2-8 V, a polishing treatment time is 20-240 s; and obtaining the biodegradable magnesium alloy nerve conduit for nerve defect repair.

Third Embodiment

A biodegradable magnesium alloy nerve conduit for nerve defect repair according to a third embodiment is illustrated, as shown in FIG. 1, which is a circular tube with a length of 5 mm, a wall thickness of 0.10 mm and an outer diameter of 1 mm; wherein the biodegradable magnesium alloy nerve conduit has 4 lines of through holes in a tube wall thereof, the through holes in each line are axially arranged along the circular tube at equal distances, and the through holes in adjacent lines are arranged in a staggered way, an amount of the through holes in each line is 5, and an aperture thereof is 0.2 mm.

A method for preparing the biodegradable magnesium alloy nerve conduit for nerve defect repair according to the third embodiment is also illustrated, wherein the method comprises steps of:

(step 1) processing a 45-degree conical surface at one end of a Mg—Nd—Zn—Zr magnesium alloy tube blank with an outer diameter of 20 mm, carrying out extrusion at a temperature of 320° C., and obtaining a magnesium alloy intermediate tube material with a size of Ø6×1 mm (outer diameter×wall thickness);

(step 2) obtaining a capillary tube with an outer diameter of 1 mm and a wall thickness of 0.10 mm after carrying out multi-pass rolling and drawing on the magnesium alloy intermediate tube material;

(step 3) carrying out stress relief annealing on the capillary tube at a temperature of 300° C. for 25 min, laser cutting and punching, and obtaining a porous conduit; and (step 4) carrying out acid pickling on the porous conduit in an ultrasound cleaning machine for 5-30 min with a pickling solution which comprises 80-100 ml/L of phosphoric acid and 40-60 g/L of ammonium bifluoride, wherein a solvent is deionized water; and then carrying out electrochemical polishing treatment at room temperature with a polishing solution which comprises phosphoric acid and absolute ethanol with a volume ratio of 1:1, wherein a polishing treatment voltage is 2-8 V, a polishing treatment time is 20-240 s; and obtaining the biodegradable magnesium alloy nerve conduit for nerve defect repair.

IMPLEMENTATION EFFECT

Figure 2:
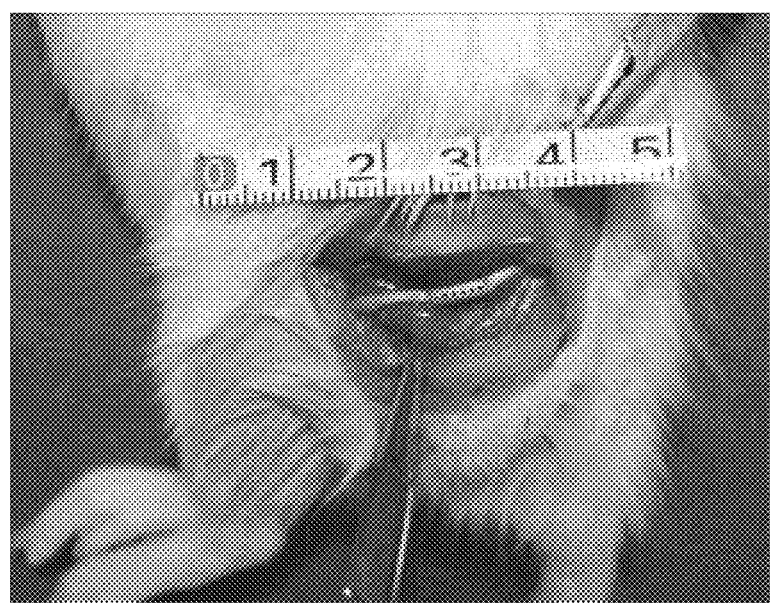
FIG. 2 is a schematic view of operation that the biodegradable magnesium alloy nerve conduit for nerve defect repair in the present invention is implanted into the 6 mm defect area of sciatic nerve of adult SD rat.
Figure 3:
FIG. 3 is a schematic view of the sciatic nerve defect area of adult SD rat after the biodegradable magnesium alloy nerve conduit for nerve defect repair in the present invention is implanted for 2 months.
Figure 4:
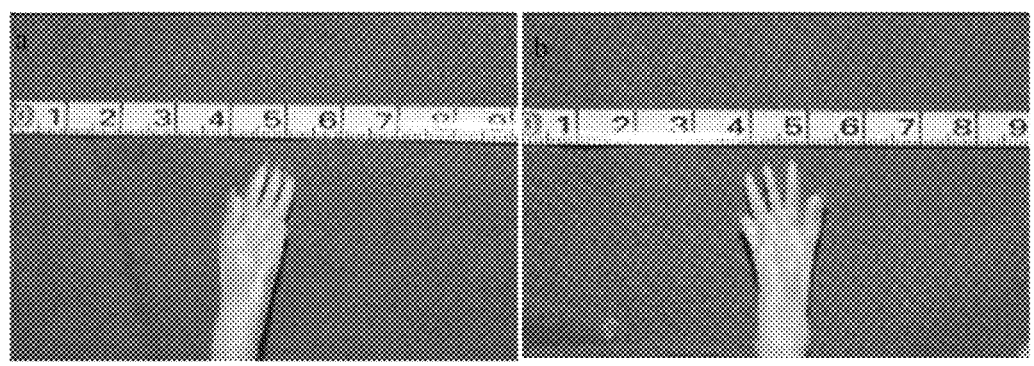
FIG. 4 is photos of toes of the rat, wherein a is the experimental side and b is the unaffected side.
Figure 5:
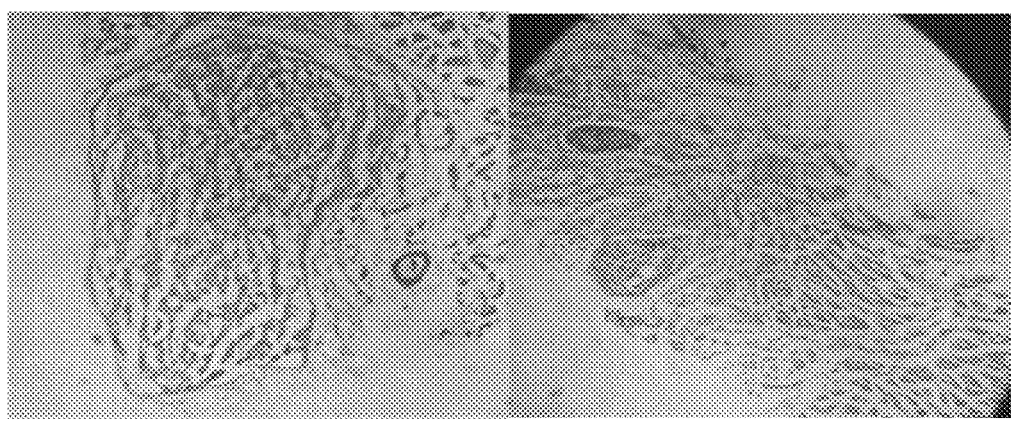
FIG. 5 is histological HE staining graphs of cross section and longitudinal section of regenerated nerve, wherein the left one is the HE staining graph of cross section of regenerated nerve; the right one is the HE staining graph of longitudinal section of regenerated nerve.

The porous biodegradable magnesium alloy nerve conduits prepared in the first, second and third embodiments are respectively implanted into the defect area of sciatic nerve of adult SD rat; the operation is shown in FIG. 2 immediately. After the nerve conduit is implanted in the rat for two months, the good nerve regeneration at the anastomotic stoma is generally observed; there is no scar tissue or inflammatory response around, and no bubble formation. Although the conduit is not completely degraded, it is softened, which confirms that the regenerated axons pass through the conduit, to achieve the purpose of nerve repair, as shown in FIG. 3. FIG. 4 is photos of toes of the rat (the left is the experimental side; the right is the unaffected side). The ulcer has healed, and there is no difference between the experimental side and the unaffected side. It indirectly confirms that the nerve axons have been well regenerated, and the nerve defects have been repaired. The histological HE staining graphs (FIG. 5) of cross section and longitudinal section of regenerated nerve confirms that there is regenerated nerve tissue in the lumen of conduit; the nerve tissue grows from proximal end to distal end through the anastomotic stoma to repair defects.

Specific embodiments of the present invention are described above. It shall be understood that the present invention is not limited to the above-mentioned specific embodiments, and those skilled in the art can make different variants and modifications within the scope of the claims, and it shall not affect the substance of the present invention.

What is claimed is:

1. A biodegradable magnesium alloy nerve conduit for nerve defect repair, wherein:
   the biodegradable magnesium alloy nerve conduit has a circular cross-sectional area, a length in a range of 5-50 mm, and a thickness in a range of 0.1-0.2 mm;
   the biodegradable magnesium alloy nerve conduit has multiple lines of through holes in a tube wall thereof, an aperture of each of the multiple lines of through holes is in a range of 0.03-0.3 mm, and a porosity of the nerve conduit is in a range of 2-20%;

each line of through holes are arranged along an axial direction of the nerve conduit at equal distances, and adjacent lines of through holes are arranged in a staggered way.

2. A method for preparing the biodegradable magnesium alloy nerve conduit for nerve defect repair according to claim 1, wherein the method comprises steps of:

(S1) processing a 45-degree conical surface at one end of a magnesium alloy tube blank, spraying boron nitride on a mold and inner and outer walls of the magnesium alloy tube blank as a lubricant, carrying out extrusion, and obtaining a magnesium alloy intermediate tube material, wherein an outer diameter of the magnesium alloy tube blank is 20 mm, an extrusion temperature is in a range of 300-400° C., an outer diameter of the magnesium alloy intermediate tube material is in a range of 6-8 mm, and a wall thickness of the magnesium alloy intermediate tube material is in a range of 0.5-1 mm;

(S2) obtaining a capillary tube after carrying out multi-pass rolling and drawing on the magnesium alloy intermediate tube material, wherein an outer diameter of the capillary tube is in a range of 1-3 mm, and a wall thickness thereof is in range of 0.1-0.2 mm;

(S3) carrying out stress relief annealing on the capillary tube, laser cutting, punching, and obtaining a porous conduit, wherein a stress relief annealing temperature is in a range of 300-350° C., and an annealing time is in a range of 20-30 min; and (S4) carrying out acid pickling on the porous conduit in an ultrasound cleaning machine with a pickling solution for 5-30 min, and then carrying out electrochemical polishing treatment with a polishing solution, and obtaining the biodegradable magnesium alloy nerve conduit for nerve defect repair, wherein the pickling solution comprises 80-100 ml/L of phosphoric acid and 40-60 g/L of ammonium bifluoride; a solvent is deionized water; the polishing solution comprises phosphoric acid and absolute ethanol with a volume ratio of 1:1 or comprises ethylene glycol monoethyl ether and hydrochloric acid with a volume ratio of 9:1; a polishing treatment voltage is in a range of 2-8 V, a polishing treatment time is in a range of 20-240 s, and a polishing treatment temperature is room temperature.

* * * * *